United States Patent [19]

Bernstein

[11] Patent Number: 5,840,734

[45] Date of Patent: Nov. 24, 1998

[54] USE OF TEMPOL IN THE PREVENTION OF PHOTOAGING

[75] Inventor: Eric Bernstein, Wynnewood, Pa.

[73] Assignee: Thomas Jefferson University, Philadelphia, Pa.

[21] Appl. No.: 851,739

[22] Filed: May 6, 1997

[51] Int. Cl.$^6$ .................................................. A61K 31/445
[52] U.S. Cl. ............................................................ 514/315
[58] Field of Search ............................................. 514/315

[56] References Cited

PUBLICATIONS

CA 118: 142604, Emerit, 1992.
BA 95: 31379, Hahn et al, 1992.
Bernstein et al., "Enhanced Elastin and Fibrillin Gene Expression in Chronically Photodamaged Skin", *J. Invest. Dermatol.* 1994, 103:182–186.
Bissett et al., "Photoprotective effect of superoxide–scavenging antioxidants against ultraviolet radiation–induced chronic skin damage in the hairless mouse", *Photodermatol. Photoimmunol. Photomed.* 1990, 7:56–62.
Chen et al., "Immunochemistry of Elastotic Material in Sun–Damaged Skin", *J. Invest. Dermatol.* 1986, 87:334–337.
Dahlback et al., "Fibrillin Immunoreactive Fibers Constitute a Unique Network in the Human Dermis: Immunohistochemical Comparison of the Distributions of Fibrillin, Vitronectin, Amyloid P Component, and Orcein Stainable Structures in Normal Skin and Elastosis", *J. Invest. Dermatol.* 1990, 94:284–291.
Frances, C. and Robert, L. "Elastin and Elastic Fibers in Normal and Pathologic Skin", *Int. J. Dermatol.* 1984, 23:166–179.
Goffman et al., "Topical Application of Nitroxide Protects Radiation–Induced Alopecia in Guinea Pigs", *Int. J. Rad. Onc. Bio. Phys.* 1992, 22:803–806.
Hsu–Wong et al., "Tissue–specific and Developmentally Regulated Expression of Human Elastin Promoter Activity in Transgenic Mice", *J. Biol. Chem.* 1994, 269:18072–18075.
Mera et al., "Elastic fibers in normal and sun–damaged skin: an Immunohistochemical study", *Br. J. Dermatol.* 1987, 117:21–27.
Mitchell et al., "Biologically Active Metal–Independent Superoxide Dismutase Mimics", *Biochem.* 1990, 29:2802–2807.
Mitchell et al., "Inhibition of Oxygen–Dependent Radiation–Induced Damage by the Nitroxide Superoxide Dismutase Mimic, Tempol", *Arch. Biochem. Biophys.* 1991, 289:62–70.
Miyachi Y., "Photoaging from an oxidative standpoint", *J. Dermatol. Sci.* 1995, 9:79–86.
Nilsson et al., "Inhibition of Lipid Peroxidation by Spin Labels", *J. Biol. Chem.* 1989, 264:11131–11135.
Samuni et al., "Superoxide Reaction with Nitroxide Spin–Adducts", *Free Radical Biol. Med.* 1989, 6:141–148.
Samuni et al., "A Novel Metal–free Low Molecular Weight Superoxide Dismutase Mimic", *J. Biol. Chem.* 1988, 263:17921–17924.
Warren et al., "Age, sunlight, and facial skin: A histologic and quantitative study", *J. Am. Acad. Dermatol.* 1991, 25:751–760.
Zimmerman et al., "Versican Is Expressed in the Proliferating Zone in the Epidermis and in Association with the Elastic Network of the Dermis", *J. Cell. Biol.* 1994, 124:817–825.

*Primary Examiner*—Rebecca Cook
*Attorney, Agent, or Firm*—Law Offices of Jane Massey Licata

[57] ABSTRACT

A method of preventing photoaging and other types of sun damage by topically applying a composition containing Tempol is provided. Pharmaceutical compositions comprising Tempol for the prevention of photoaging and other types of sun damage are also provided.

5 Claims, No Drawings

USE OF TEMPOL IN THE PREVENTION OF PHOTOAGING

BACKGROUND OF THE INVENTION

The effects of ultraviolet radiation from exposure to the sun on human skin are a growing concern for today's longer-lived population. The majority of changes associated with an aged appearance result from chronic sun-damage. Warren et al., *J. Am. Acad. Dermatol.* 1991, 25:751–760; Frances, C. and Robert, L., *Int. J. Dermatol.* 1984, 23:166–179. Dramatic alterations of the superficial dermis accompany the deep wrinkles and laxity common in photoaged skin. The major histopathologic alteration of photoaged skin is the accumulation of material which, on routine histopathologic examination, has the staining characteristics of elastin and is, thus, termed solar elastosis. Immunohistochemical staining has shown the poorly-formed fibers comprising solar elastosis to be composed of elastin (Chen et al., *J. Invest. Dermatol.* 1986, 87:334–337; Mera et al., *Br. J. Dermatol.* 1987, 117:21–27) fibrillin (Chen et al., *J. Invest. Dermatol.* 1986, 87:334–337; Dahlback et al., *J. Invest. Dermatol.* 1990, 94:284–291; Bernstein et al., *J. Invest. Dermatol.* 1994, 103:182–186) and versican, the normal components of elastic fibers (Zimmerman et al., *J. Cell. Biol.* 1994, 124:817–825). A coordinate increase in elastin, fibrillin and versican mRNAs has been demonstrated in fibroblasts derived from photodamaged skin, as compared to fibroblasts derived from normal skin from the same individuals. Bernstein et al., *J. Invest. Dermatol.* 1994, 103:182–186. Elevated elastin mRNA levels in sundamaged skin result from enhanced elastin promoter activity, as shown by transient transfections of fibroblasts with a DNA construct composed of the human elastin promoter linked to the chloramphenicol acetyltransferase (CAT) reporter gene. Bernstein et al., *J. Invest. Dermatol.* 1994, 103:182–186.

The generation of free radicals following exposure of the skin to ultraviolet radiation is well known in the art. Free radical mechanisms have been shown to be responsible for redness and erythema resulting from exposure to ultraviolet radiation. A number of antioxidants have been tested as photoprotective agents, however, results from these studies indicate that the ability of these agents to provide protection is variable.

Miyachi Y., *J. Dermatol. Sci.* 1995, 9:79–86 provides a review of photoaging from a photo-oxidative standpoint and suggests the use of antioxidants as regulators of photoaging. Specifically, studies with superoxide dismutase (SOD) are described. However, it is concluded that sunscreen agents provided better protection from ultraviolet radiation.

Bissett et al. *Photodermatol. Photoimmunol. Photomed.* 1990, 7:56–62 demonstrated that mice, topically treated with solutions of superoxide-scavenging anti-oxidants such as alpha-tocopherol, ascorbic acid, propyl galate and Trolox prior to ultraviolet B (UVB) radiation exposure, exhibited significantly less damage than untreated mice. However, additional antioxidants or free radical scavengers that were tested, including glutathione, beta-carotene, BHT, mannitol, divinylglycol, pantetheine, urea and histidine, provided no significant protection against UVB radiation. Further, the severity of UVA radiation-induced mouse skin damage was not reduced by topical application of these antioxidants in these studies. Thus, it is clear that the current approaches used to prevent the cumulative effects of photoaging are inadequate.

Historically, more research has been done in the area of radiation oncology. Damage from ionizing radiation and a portion of ultraviolet radiation-induced damage has been shown to be due to the formation of radical oxygen species. Sulfhydryl compounds were among the first radioprotectors to be identified. Their protective mechanism appears to be due to their ability to scavenge radiation-induced free radicals and/or donate reducing equivalents to oxidized molecules. Hematopoietic cytokines have also been investigated as radioprotectors. They are believed to protect by more quickly restoring hematopoietic function after radiation exposure.

Recently, a new class of radioprotectors, the nitroxides, has been described. As a class, nitroxides are stable free radical components which react with a variety of biologically relevant compounds including other free radicals (Nilsson et al. *J. Biol. Chem.* 1989, 264:11131–11135). The observation that several nitroxides themselves reacted with free radicals, specifically oxy radicals, led to the investigation of these compounds as radioprotectors (Samuni et al. *Free Radical Biol. Med.* 1989, 6:141–148).

Tempol [4-hydroxy-2,2,6,6-tetramethyl-piperidinyloxy, free radical] is a piperidinyl-n-oxyl with the n-oxide sterically stabilized by symmetric pairs of adjacent methyl groups. This compound is commercially available through Aldrich Chemical Co., Milwaukee, Wis. It is most commonly used to spin label biological molecules such as NADP.

Tempol has been demonstrated to function as a superoxide dismutase (SOD) mimic, protecting mammalian cells from superoxide generated from hypoxanthine/xanthine oxidase and from hydrogen peroxide mediated cytotoxicity (Mitchell et al. *Biochem.* 1990, 29:2802–2807; Samuni et al. *J. Biol. Chem.* 1988, 263:17921–17924). Tempol has also been demonstrated to provide both in vitro and in vivo protection against ionizing radiation (Mitchell et al. *Arch. Biochem. Biophys.* 1991, 289:62–70). Recently, Tempol was shown to protect against radiation induced alopecia by speeding the recovery of hair growth within a field of heavily irradiated skin (Goffman et al. *Int. J. Rad. Onc. Biol. Phys.* 1992, 22:803–806). Goffman et al. suggest that this protection is due to direct protection of hair follicle stem cells and development of other nitroxides. Importantly, this study also demonstrated that Tempol is undetectable in the blood following application. This is of concern because topical radioprotectors share a tendency towards systemic absorption, raising the potential problem of tumor radioprotection.

It has now been found that topical application of Tempol prevents photoaging and other skin damage resulting from exposure to ultraviolet radiation.

SUMMARY OF THE INVENTION

In the present invention, a new use is provided for the compound Tempol (4-hydroxy-TEMPO, free radical; 4-hydroxy-2,2,6,6-tetramethylpiperidinyloxy, free radical). It has now been found that Tempol prevents photoaging and blocks UVR thereby preventing other sun-damage such as sunburn or skin cancer. In addition, Tempol has now been shown to protect against UVA in vitro. This compound not only functions as a free-radical scavenger, but also possesses sun blocking ability. The ability to block ultraviolet radiation-induced damage has been demonstrated. Compositions for use as sunscreen agents comprising Tempol are also provided.

DETAILED DESCRIPTION OF THE INVENTION

Profound changes take place in the superficial dermis as a result of chronic sun-exposure. The major alteration is the deposition of massive amounts of abnormal elastic material, termed solar elastosis. It has been shown that solar elastosis is accompanied by elevations in elastin and fibrillin mRNAs and elastin promoter activity.

A transgenic mouse model which contains the human elastin promoter linked to a chloramphenicol acetyltransferase (CAT) reporter gene for testing compounds that may inhibit cutaneous photodamage has been developed. These mice express human elastin promoter activity in a tissue-specific and developmentally regulated manner. Promoter activity can be studied in this model as a function of small increases in ultraviolet radiation, demonstrating the sensitivity of the assay. In addition, quantitative data can be obtained after only a single exposure to ultraviolet radiation. A test compound is applied to the skin of a transgenic mouse capable of expressing the human elastin promoter. The transgenic mouse is then exposed to ultraviolet radiation and human elastin promoter activity in the mouse is determined. The human elastin promoter activity is then compared to that in transgenic mice also exposed to an equivalent dose of ultraviolet radiation which were not treated with the test compound to determine whether or not the test compound provided protection against the ultraviolet radiation. Since elastin promoter activation is a primary event in cutaneous aging, these mice represent a mouse model of human photoaging.

Using this transgenic mouse line, the ability of Tempol to inhibit the effects of ultraviolet radiation on human elastin promoter activity was determined. In these experiments, 4–5 day old mice received either no treatment, 0.4M Tempol, 245 mJ/cm$^2$ UVB, or 245 mJ/cm$^2$ UVB and 0.4M Tempol. Tempol was diluted in ethanol and was applied topically to the backs of these mice. Following phototreatment, the backs of the mice were rinsed twice with 70% isopropyl alcohol pads to remove any excess Tempol. Mice were sacrificed and skin harvested for determination of CAT activity 24 hours after phototreatment. Tempol alone produced no significant change, raising CAT activity 1.7 fold (s.d.=0.48). UVB increased CAT activity 7.2-fold (standard deviation (s.d.)=0.72), and the addition of Tempol to UVB-treated mice decreased the elevation to 3.3-fold (s.d.=0.68) that of untreated controls.

Experiments demonstrating the ability of Tempol to protect against UVB-induced promoter activation were also performed in fibroblast cultures established from the skin of transgenic mice. Cells received either no Tempol or UVB (controls) 50 mM Tempol alone without UVB, 5.5 mj/cm$^2$ UVB alone, pretreatment with 25 mM Tempol and subsequent exposure to 5.5 mJ/cm$^2$ UVB, or pretreatment with 50 mM Tempol and subsequent exposure to 5.5. mJ/cm$^2$ UVB. Tempol was added to culture dishes ten minutes prior to exposure to UVB and left on the cells 4 minutes after UVB exposure. Tempol alone did not alter CAT activity in these cells to a significant degree. UVB alone increased CAT activity to 9.5-fold (s.d.=0.47) that of unirradiated cells. The addition of 25 mM Tempol to UVB-treated cells decreased the elevation to 4.2-fold (s.d.=0.02) that of controls, while 50 mM Tempol further decreased the elevation to 2.8-fold (s.d.=1.4) that of controls.

Additional experiments were performed in cells with varying amounts of UVB. In these experiments, control cells received no UVB or Tempol. UVB controls received either 0.7, 1.4, 2.7 or 5.5 mJ/cm$^2$ of UVB. Tempol controls received 100 mM of Tempol and no UVB. UVB treated cells were preincubated with phosphate buffered saline (PBS) or 100 mM Tempol 12.5 minutes before UVB. The effect of UVB and Tempol on cell viability was determined using a tryptan blue exclusion kit.

Before application to cultures, tissue culture medium was removed and the cells were rinsed twice with PBS. Cells were incubated in 10 cm diameter dishes with 3 ml of 100 mM Tempol or PBS for 12.5 minutes prior to UVB exposure. UVB controls were placed in an equal amount of PBS 12.5 minutes prior to irradiation with UVB. After treatment, cells were cleansed twice with PBS and the tissue culture medium was replaced in all dishes. Cells were harvested for determination of CAT activity 24 hours after phototreatment. Only fibroblasts from mice representing the same litter were used for any given experiment, and utilized in passage two to three times. Two dishes of cells were used for each data point, and experiments were repeated in triplicate. Thus, six values were determined for each experimental condition. For statistical analysis, a paired t-test was performed. Data from these experiments is depicted in Table 1.

TABLE 1

| In Vitro Effect of Tempol on UVB-induced induction of CAT activity | | | |
|---|---|---|---|
| UVB Dose (mJ/cm$^2$) | UVB CAT | UVB + Tempol CAT | % Protection from UVB |
| 0.7 | 3.2 | 1.9 | 41 $p < 0.01$ |
| 1.4 | 8.1 | 2.1 | 74 $p < 0.001$ |
| 2.8 | 15.7 | 4.8 | 69 $p < 0.001$ |
| 5.5 | 20.0 | 11.6 | 42 $p < 0.001$ |

As in previous experiments, Tempol alone did not alter CAT activity to a significant degree (1.2-fold that of untreated cells). UVB alone increased CAT activity 3.2-, 8.1-, 15.7- and 20.0-fold that of control cells for UVB doses of 0.7, 1.4, 2.7 and 5.5 mJ/cm$^2$ of UVB, respectively. The addition of 100 mM Tempol to UVB-treated cells decreased this elevation to 1.9-, 2.1-, 4.8- and 11.6-fold greater than untreated controls for UVB doses of 0.7, 1.4, 2.7 and 5.5 mJ/cm$^2$ of UVB, respectively.

The free radical scavenging ability of Tempol was also demonstrated in cells. Cells received either no treatment, 5.5 mJ/cm$^2$ of UVB, UVB with 50 mM Tempol suspended in an quartz dish above the cells covered in saline, or UVB with 50 mM Tempol applied directly to the cells with saline in a quartz dish suspended above the cells. Tempol suspended above the cells functions as a UVB blocker. Tempol applied directly to the cells functions as both a UVB blocker and a scavenger of free radicals. UVB alone resulted in a 14.2-fold (s.d.=1.5) increase in CAT activity. Tempol suspended above the cells in a quartz dish (and thus acting as a screen only) resulted in a 2.4-fold increase in CAT activity as compared to untreated controls, which is almost a 6-fold reduction from cells treated with UVB alone and not receiving Tempol, thus demonstrating significant protection from UVB. When Tempol was placed in direct contact with cells, CAT activity was reduced to 1.5-fold that of controls. Accordingly, the scavenging properties of Tempol reduced CAT activity a further 38%. Thus, in addition to providing protection against photoaging by absorbing light, Tempol has also been demonstrated to offer protection against damage once ultraviolet radiation has already reached the skin.

Experiments demonstrating the ability of Tempol to protect against UVA-induced promoter activation were also performed in fibroblast cultures established from the skin of transgenic mice. Because a response to UVA alone in vitro is not measurable and the in vivo response is relatively small, 8-methoxypsoralen (8-MOP) was added to the system to enhance the promoter response to UVA. The addition of 8-MOP resulted in a substantial increase in CAT activity following administration of UVA, making this model more useful for studying agents which may protect against UVA as well as UVB.

In these experiments, control cells received no UVA or 8-MOP. UVA controls received either 0.5, 0.75 or 1.0 J/cm$^2$ of UVA without prior incubation with 8-MOP. 8-MOP controls received 1 µg/ml of 8-MOP but no UVA. Tempol controls received. 100 mM Tempol and no UVA or 8-MOP. PUVA-treated cells were preincubated with 1.0 µg/ml of 8-MOP in PBS and then exposed to 0.5, 0.75 or 1.0 J/cm$^2$. Tempol treated cells were pretreated with 100 mM Tempol 12.5 minutes prior to UVA exposure. 8-MOP was also added to these cells at the same time as the Tempol.

It was found that the combination of 1 µg/ml of 8-MOP and 0.5, 0.75 or 1.0 J/cm$^2$ of UVA in fibroblast cultures resulted in increases in CAT activity to 2.7-, 9.0- and 21.4-fold that of controls, respectively. UVA alone and 8-MOP alone failed to produce significant CAT activity. The addition of Tempol to the cultures reduced the PUVA-induced increase in CAT activity to 1.5-, 1.2- and 2.0-fold that of controls, respectively, thus almost completely eliminating the PUVA-induced increase in CAT activity. The absorption spectrum of Tempol has shown very little absorption in the UVA range, making the protection by Tempol against PUVA-induced elastin gene induction almost entirely due to the free radical scavenging abilities of Tempol. In addition, suspending Tempol above the cells failed to afford protection against the PUVA-induced increases in CAT activity, thus further demonstrating that protection by Tempol against UVA-induced photodamage is almost entirely due to its free radical scavenging properties.

Accordingly, topical application of a composition comprising Tempol to the skin provides protection against photoaging and other sun-damage such as sunburn and skin cancer. Examples of compositions comprising Tempol include, but are not limited to creams, lotions and sprays. Methods of formulating Tempol into creams, lotions and sprays as well as pharmaceutical additives for such formulations are well known to those skilled in the art. As will be obvious to those skilled in the art upon this disclosure, such compositions may further comprise secondary or additional sunscreens or free radical scavengers such as, but not limited to, Vitamin C and Vitamin E and analogs thereof. In a preferred embodiment, a composition comprising Tempol is applied to the skin prior to exposure to the sun. However, application of these compositions subsequent to the exposure can also mitigate any damage resulting to the skin from this exposure. It is believed that these compositions of the present invention will be especially useful in protecting individuals with heightened sensitivities to the sun, such as, but not limited to, individuals undergoing psoralen treatment for cancer, psoriasis and other skin conditions; individuals undergoing photodynamic therapy for skin cancer, psoriasis and other skin conditions; individuals suffering from genetic repair defects such as xeroderma pigmentosa, albinism or other conditions resulting from decreased endogenous melanin pigment.

The following nonlimiting examples are provided to further illustrate the present invention.

EXAMPLES

Example 1

Transgenic Mice Expressing the Human Elastin Promoter

A homozygous line of transgenic mice expressing the 5.2-kb human elastin promoter linked to a CAT reporter gene was used. Hsu-Wong et al., *J. Biol. Chem.* 1994, 269:18072–18075. These mice express the human elastin promoter in a tissue-specific and developmentally regulated manner. Mice four or five days old were used since at this age, visible hair growth is not yet present.

Example 2

Fibroblast Cultures

Fibroblast cultures were established from the skin of transgenic mice by explanting tissue specimens onto plastic tissue culture dishes and allowing cells to migrate to the surrounding area. The primary cultures were maintained in Dulbecco's modified Eagle's medium supplemented with 10% fetal calf serum, 2 mM L-glutamine and antibiotics, at 37° C. The primary cell cultures were passaged by trypsinization, and the subcultures in passages three or four were utilized for UVB treatment. After UV exposure, the cells were incubated in tissue culture medium for 24 hours, and then harvested for determination of CAT activity.

Example 3

CAT Assay

To measure the expression of the human elastin promoter/CAT reporter gene construct in the skin of transgenic mice and in fibroblast cultures established from these animals, CAT activity was determined. For extraction of the CAT from skin, the specimens were homogenized in 0.25 Tris-HCl, pH 7.5, using a tissue homogenizer (Brinkmann Instruments, Inc. Westbury, N.Y.). The homogenates were centrifuged at 10,000 X g for 15 minutes at 4° C. and the protein concentration in the supernatant determined by a commercial protein assay kit (Bio-Rad Laboratories, Richmond, Calif.). Aliquots of the supernatant containing 100 µg of protein were used for assay of CAT activity by incubation with [$^{14}$C] chloramphenicol in accordance with well-known procedures. The acetylated and non-acetylatecd forms of radioactive chloramphenicol were separated by thin-layer chromatography and CAT activity was determined by the radioactivity in the acetylated forms as a percent of the total radioactivity in each sample.

Example 4

UVB Sources

Irradiation with UVB for in vitro and in vivo studies were performed using a closely spaced array of seven Westinghouse FS-40 sunlamps, which delivered uniform irradiation at a distance of 38 cm. The energy output at 38 cm was measured with a Solar Light Model 3D UVA and UVB detector (Solar Light Company, Philadelphia, Pa.). The output of FS-40 sunlamps was 23.4 units/hour of UVB at 38 cm, where each unit is equivalent to 21 mJ/cm$^2$ or erythema effective energy.

Example 5

UVA Sources

Irradiation with UVA was performed using a closely spaced array of seven Sylvania FR40T12 PUVA lamps filtered through window glass of 2 mm thickness to remove wavelengths below 320 nm. The energy output at 38 cm from the array was measured with a Solar Light Model 3D UVA and UVB detector (Solar Light Company, Philadelphia, Pa.). The output of the lamps filtered through the window glass was 2.02 mW/cm$^2$, with no detectable UVB.

What is claimed:

1. A method of protecting humans exposed to sunlight against photoaging, sunburn and skin cancer comprising topically applying to skin of a human tempol in an amount effective to protect the skin against photoaging, sunburn and skin cancer.

2. The method of claim 1 wherein the tempol is applied prior to exposure of the skin to sunlight.

3. The method of claim 1 wherein the tempol is applied subsequent to exposure of the skin to the sun.

4. A method of protecting individuals with a heightened sensitivity to the sun from damage resulting from the sun comprising topically applying to the skin of an individual with a heightened sensitivity to the sun tempol in an amount effective to protect the skin against photoaging sunburn and skin cancer prior to exposure of the individual to the sun.

5. A pharmaceutical composition of claim comprising tempol and a second sunscreen and a pharmaceutical additive.

* * * * *